United States Patent [19]
Blosser et al.

[11] Patent Number: 5,247,118
[45] Date of Patent: Sep. 21, 1993

[54] CONTINUOUS SODIUM PHENATE-CATALYZED TRANSESTERIFICATION PROCESS FOR MAKING PHOSPHITE ESTERS

[75] Inventors: Robert C. Blosser; John F. Gurcsik, both of Morgantown; Charles E. White, Jr., Arthurdale, all of W. Va.

[73] Assignee: General Electric Company, Pittsfield, Mass.

[21] Appl. No.: 829,128

[22] Filed: Jan. 31, 1992

[51] Int. Cl.$^5$ ............................................. C07F 9/141
[52] U.S. Cl. ...................................... 558/118; 558/119
[58] Field of Search ................................ 558/118, 119

[56] References Cited

U.S. PATENT DOCUMENTS

| | | | |
|---|---|---|---|
| 3,047,608 | 7/1962 | Friedman et al. | 558/78 |
| 3,205,250 | 9/1965 | Hechenbleikner | 558/78 |
| 3,326,939 | 6/1967 | Guttag | 549/222 |
| 3,354,241 | 11/1967 | Larrison | 558/156 |
| 3,437,720 | 4/1969 | Guttag | 558/78 |
| 4,290,976 | 9/1981 | Hechenbleikner et al. | 558/78 |
| 4,692,540 | 9/1987 | Illy et al. | 558/78 |
| 4,739,090 | 4/1988 | Tajima et al. | 558/78 |

OTHER PUBLICATIONS

Organic Phosphorous Compounds VS, Kosolapoff Maier 1973, pp. 39 and 40.

*Primary Examiner*—Mary C. Lee
*Assistant Examiner*—Michael G. Ambrose

[57] ABSTRACT

A process for making phosphite esters is provided. The process involves reacting triphenyl phosphite with alcohol using a sodium phenate catalyst. The process yields high purity phenol which may be recycled and reacted with PCl$_3$ to yield triphenyl phosphite.

4 Claims, No Drawings

CONTINUOUS SODIUM PHENATE-CATALYZED TRANSESTERIFICATION PROCESS FOR MAKING PHOSPHITE ESTERS

BACKGROUND OF THE INVENTION

1. Field of the Invention

This invention relates to a process for making phosphite esters and more particularly relates to a process for making phosphite ester by reacting triphenyl phosphite with an alcohol in the presence of a catalyst.

2. Description of the Related Art

Production of phosphite ester by reacting phosphites with alcohols in the presence of alkaline catalysts such as sodium methylate, sodium decylate, sodium phenolate or potassium cresylate are known, see Guttag U.S. Pat. No. 3326939, Guttag U.S. Pat. No. 3437720, Friedman et al U.S. Pat. No. 3047608, and Hechenbleikner U.S. Pat. No. 3205257, all of which are incorporated herein by reference.

These processes can however result in the production of catalyst related impurities. For example, reacting triphenyl phosphite (TPP) with various alcohols using sodium methylate catalyst results in phenol distillate containing several catalyst-related impurities such as methanol, anisole, and water. These impurities result in reduced purity of the recovered phenol and less-pure phosphite esters, and require purification of the recovered phenol before reuse in manufacture of triphenyl phosphite.

When sodium methylate is used as a catalyst in reactions of triphenyl phosphite with alcohols, the sodium methylate produces sodium phenate, the actual reaction catalyst, but it also causes the formation of undesirable by-products.

Sodium methylate reacts with phenol to form sodium phenate and methanol, with the sodium phenate remaining as the actual reaction catalyst. The methanol reacts with phenol to produce anisole and water.

Anisole is relatively stable but remains as an impurity in the phenol distillate and the phosphite. Water reacts with phosphites to produce acidic phosphite compounds, thereby increasing the acid number and giving a less pure product. The less-pure product results in decreased filtration rates, primarily due to diphosphites formed from the reaction of phosphite and water.

Consequently, there is a need to provide a process which results in higher purity phenol distillate and higher purity product.

SUMMARY OF THE INVENTION

The present invention involves the reaction of triphenyl phosphite with alcohols using a sodium phenate catalyst. The process provides a high purity phenol distillate and a high purity product.

DETAILED DESCRIPTION OF THE INVENTION

It has now been found that a high purity phenol distillate can be attained by transesterification of triphenyl phosphite (TPP) with an alcohol using sodium phenate as the catalyst. The sodium phenate catalyst or the like is preferably used in an amount of 0.1 to 1% by weight based on the total weight of the triphenyl phosphite. The catalyst has the formula

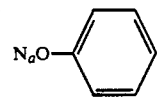

Replacement of sodium methylate with sodium phenate in the reaction is expected to greatly reduce the methanol formation and thus reduce the anisole and water formation in the phosphite phenol distillate. Since this distillate is recycled to produce triphenyl phosphite, this is expected to result in a purer triphenyl phosphite with an increase in the amount of phosphite product produced per pound of original triphenyl phosphite added, and an increase in the number of triphenyl phosphite phenol distillate recycles. Phenol distillate from triphenyl phosphite (the amount used in excess of the stoichiometric requirement) is reused in triphenyl phosphite.

The transesterification is carried out by distilling out the phenol by heating the reaction mixture under reduced pressure, preferably 10-29 mm mercury. The transesterification can also be controlled by the amount of phenol being removed or by limiting the amount of alcohol which is added, for example, by adding one, two or three mols of monohydric alcohol per mol of triaryl phosphite, or by adding for each mol of triphenyl phosphite either one mol or 1.5 mols of glycol. The time necessary for anisole, methanol, and the phenol carry-over to be distilled is decreasd with the use of sodium phenate catalyst.

Mixed phosphite esters can also be prepared by a two step reaction. For example, one mol of pentaerythritol can be reacted with two mols of triphenyl phosphite and one mol of the 3,9-diphenoxy 2,4,8,10-tetraoxa-3,9-diphosphaspiro (5,5) undecane thus formed can then be reacted with two mols of a monohydric alcohol, e.e., decyl alcohol, to form the corresponding 3,9-didecyloxy compound. The sodium phenate catalyst present in this first step of the reaction also serves in the second step of the reaction.

The preferred alcohols are alkanols, 1,2- alkanediols, 1,3-alkanediols, pentaterythritol, and monoalkyl ethers of ethylene glycol and polyethylene glycol. In making bis dioxaphosphorinanes the use of polyethylene glycol, polypropylene glycol, thiodiglycol and sulfonyldiglycol are useful for forming the bridge between the two dioxaphosphorinane rings.

As the alcoholic reactant there can be used methyl alcohol, butyl alcohol, tetrahydrofurfuryl alcohol, n-octanol, 2-ethyl hexanol, isoctyl alcohol, n-decyl alcohol, isodecyl alcohol, lauryl alcohol, tridecyl alcohol, myristyl alcohol, cetyl alcohol, stearyl alcohol, cyclohexanol, alkanediols or glycols such as ethylene glycol, propylene glycol, trimethylene glycol, 1,2-butylene glycol, 2,3-butylene glycol, pinacol, 1,2-pentanediol, hexylene glycol (2-methyl-2,4 pentanedoil), 1,3-butylene glycol, neopentyl glycol, 2-ethyl-1,3-hexenediol, 2,4-pentanedoil, 2,4-heptanediol, 2,2-diethyl-1,3-propanediol, 2-ethyl-2-n-butyl-1,3-propanediol, neohexylene glycol, (2-ethyl-2-methyl-1,3-propanediol), monoalkyl monoaryl ethers of alkanedoils, e.g. methyl ether of ethylene glycol, ethyl ether of ethylene glycol, butyl ether of ethylene glycol, methyl ether of diethylene glycol, ethyl ether of diethylene glycol, butyl ether of diethylene glycol, methyl ether of polyethylene glycol of molecular weight 300-350, ethyl ether of polyethylene glycol of molecular weight of 300–350, methyl ether of polyethylene glycol of molecular weight 550, methyl ether of polyethylene glycol of molecular weight 4000, methyl ether of triethylene glycol, phenyl ether of ethylene glycol.

Suitable monophosphite produced include those represented by the general formula:

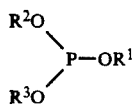

wherein $R^1$, $R^2$ and $R^3$ represent either equal or different hydrocarbyl radicals, which can be either substituted or non-substituted alkyl, cycloalkyl, aryl, alkaryl or aralkyl radicals.

In particular, trialkyl phosphites, dialkyl monophenyl phosphites, diphenyl monoalkyl phosphites and triphenyl phosphites, possibly bearing hydrocarbyl substituents on the benzene ring, are known and used in the art.

Specific examples of such organic phosphites are: diphenyl 2-ethylhexyl phosphite, triphenyl phosphite, tris(2,5-di-tert.-butyl-phenyl)phosphite, tris(2-tert.-butylphenyl)phosphite, tris(2-phenylphenyl)phosphite, tris{2-(1,1-dimethylpropyl)phenyl}phosphite, tris(2-cyclohexylphenyl)phosphite, tris(2-tert.-butyl-4-phenylphenyl)phosphite, tris)2-tert.-butyl-4-methylphenyl)phosphite, tris(2,4-di-tert.-amylphenyl)phosphite and tris(2,4-di-tert.-butylphenyl)phosphite.

Another class of organic phosphites which can be made according to the present invention is definable by means of the general formula:

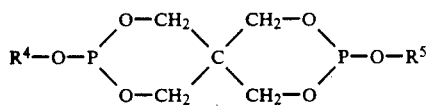

wherein: $R^4$ and $R^5$ radicals, equal to, or different from, each other, represent hydrocarbyl radicals, which can be either substituted or non-substituted alkyl, cycloalkyl, aryl, alkaryl or aralkyl radicals.

Specific examples of such suitable organic phosphites are: bis(2,4-di-tert.-butylphenyl)pentaerythritol diphosphite and distearyl pentaerythritol diphosphite. The continuous process of the present invention may be illustrated as follows. Note that the TPP is recycled to the first step for reaction with the alcohol. The present continuous process which uses sodium phenate as the catalyst rather than sodium methylate, provides reduced impurities that could build up in the TPP over time as it is recycled, for example 10 or 20 or 40 times, depending on the buildup of impurities.

TPP + alcohol + sodium phenate ⟶

⟶ organic phosphite + phenol + sodium phenate ⟶

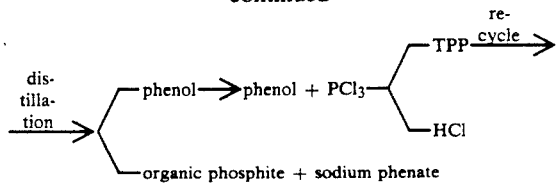

The following examples are illustrative and not limitative of the purview of the present invention.

Examples
PROCESS FOR MAKING PHOSPHITE ESTERS

| CHARACTERISTIC | SODIUM METHYLATE CATALYST | SODIUM PHENATE CATALYST |
|---|---|---|
| PHENOL DISTILLATE PURITY time necessary to distill anisole, methanol, & phenol carryover per lb. of produced ester (hrs/lb. produced ester) | 0.0125 | 0.0095 |
| PHENOL DISTILLATE PURITY, from phosphite ester reaction | 99–100% Phenol 0–1% Alcohol 0.2% Anisole 0.1% Methanol 0.0% Water* | 99–100% Phenol 0–1% Alcohol 0% Anisole 0% Methanol 0% Water |
| PHOSPHITE ESTER PURITY, TDP % di-decyl phosphite | 0.2–1.3% | <0.1% |
| PHOSPHITE ESTER PURITY, ODPP | 2.8 | 1.7 |
| filtration time, hrs. TLP | 11.3 | 7.2 |
| DPDP | 2.1 | 1.3 |
| TPP PURITY, reftactive index | 1.5885** | 1.5888 |
| TPP PURITY, acid number | 0.15** | 0.13 |
| PHENOL DISTILLATE PURITY, from TPP reaction-number of consecutive phenol recycles | 20** | 40 |
| PHOSPHITE ESTER YIELD, PDDP | 1.4** | 1.5 |
| lbs ester produced per DPDP lb TPP charged | 1.1** | 1.2 |

*Water reacts with phosphite to produce di-phosphite
**Expected values only (no data)
TDP = tri-decyl phosphite
ODPP = octyl, di-phenyl phosphite
TLP = tri-lauryl phosphite
DPDP = di-phenyl, decyl phosphite
TPP = tr-phenyl phosphite
PDDP = phenyl, di-decyl phosphite

We claim:
1. A continuous process for making an organic phosphite, said process consisting of:
   a) adding a sodium phenate to a reaction process stream to catalyze the reaction of triphenyl phosphite with an alcohol to produce an organic phosphite and phenol,
   b) separating said phenol from said organic phosphite by distillation,
   c) reacting said distilled phenol with phosphorous trichloride to produce triphenyl phosphite and hydrochloric acid,
   d) separating said triphenyl phosphite from said hydrochloric acid, and
   e) recycling said triphenyl phosphite into step a.
2. The process of claim 1 wherein said organic phosphite has an acid number of less than 0.01 mg KOH/g phosphite.
3. The process of claim 1 wherein said distilled phenol is free of anisole.
4. The process of claim 1 wherein said phosphite is essentially free of water.

* * * * *